(12) United States Patent
Desmond et al.

(10) Patent No.: US 6,835,837 B2
(45) Date of Patent: Dec. 28, 2004

(54) PROCESS FOR MAKING SUBSTITUTED 8-ARYLQUINOLINIUM BENZENESULFONATE

(75) Inventors: Richard Desmond, Bridgewater, NJ (US); David A. Conlon, Plainsboro, NJ (US); Antoinette Drahus, Hoboken, NJ (US); Guo-Jie Ho, Scotch Plains, NJ (US); Brenda Pipik, Edison, NJ (US); Carl Leblond, Gilbertsville, PA (US); Anant Vailaya, North Brunswick, NJ (US)

(73) Assignee: Merck & Co. Inc., Rahway, NJ (US)

( * ) Notice: Subject to any disclaimer, the term of this patent is extended or adjusted under 35 U.S.C. 154(b) by 0 days.

(21) Appl. No.: 10/433,538

(22) PCT Filed: Dec. 14, 2001

(86) PCT No.: PCT/US01/48385

§ 371 (c)(1),
(2), (4) Date: May 15, 2003

(87) PCT Pub. No.: WO02/060897

PCT Pub. Date: Aug. 8, 2002

(65) Prior Publication Data

US 2004/0044213 A1 Mar. 4, 2004

Related U.S. Application Data

(60) Provisional application No. 60/256,799, filed on Dec. 20, 2000.

(51) Int. Cl.$^7$ ................. C07D 413/10; C07D 215/12

(52) U.S. Cl. ............. 546/167; 546/172; 546/173; 514/314; 514/311; 514/256

(58) Field of Search ................. 546/167, 172, 546/173; 514/314, 311, 256

(56) References Cited

U.S. PATENT DOCUMENTS

| 4,006,137 A | 2/1977 | Haugwitz et al. |
|---|---|---|
| 6,410,563 B1 * | 6/2002 | Deschenes et al. ......... 514/314 |
| 6,740,566 B2 | 5/2004 | Lyons |
| 2002/0143032 A1 * | 10/2002 | MacDonald |

FOREIGN PATENT DOCUMENTS

| WO | WO 95/35283 | 12/1995 |
|---|---|---|
| WO | WO 99/37622 | 7/1999 |
| WO | W0 01/46151 A1 | 6/2001 |
| WO | WO 02/069970 | 9/2002 |

OTHER PUBLICATIONS

Salt selection for Basis drugs, Philip Gould 1986, vol.33, pp. 201–217.*
Rangnekar, et al., Dyes and Pigments vol. 45, No. 2, pp. 87–96 (2000).
International Journal of Pharmaceutics, 33 (1986) 201–217.

* cited by examiner

Primary Examiner—Rita Desai
(74) Attorney, Agent, or Firm—Curtis C. Panzer; David L. Rose

(57) ABSTRACT

A substituted 8-aryl quinoline and its benzenesulfonic acid salt is synthesized.

2 Claims, 5 Drawing Sheets

PROCESS FOR MAKING SUBSTITUTED 8-ARYLQUINOLINIUM BENZENESULFONATE

RELATED APPLICATION DATA

This is a National filing under 35 USC 371 of PCT/US 01/48385, filed Dec. 14, 2001, which claims priority from U.S. Ser. No. 60/256,799, filed Dec. 20, 2000.

BACKGROUND OF THE INVENTION

1. Field of the Invention

The present invention is directed to a process to make the benzenesulfonic acid salt of a substituted 8-arylquinolines. In particular, this invention is directed to a process to make 6-[1-methyl-1-(methylsulfonyl)ethyl]-8-[3-[(E)-2-[3-methyl-1,2,4-oxadiazol-5-yl]-2-[4(methylsulfonyl)phenyl]ethenyl]phenyl]quinolinium benzenesulfonate which is a phosphodiesterase-4 inhibitor.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3', 5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3', 5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

Compounds that inhibit PDE4 activity are useful in the treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues. A major concern with the use of PDE4 inhibitors is the side effect of emesis which has been observed for several candidate compounds as described in C. Burnouf et al., ("Burnouf"), Ann. Rep. In Med. Chem., 33:91–109(1998). B. Hughes et al., Br. J. Pharmacol., 118:1183–1191(1996); M. J. Perry et al., Cell Biochem. Biophys., 29:113–132(1998); S. B. Christensen et al., J. Med. Chem., 41:821–835(1998); and Burnouf describe the wide variation of the severity of the undesirable side effects exhibited by various compounds. As described in M. D. Houslay et al., Adv. In Pharmacol, 44:225–342(1998) and D. Spina et al., Adv. In Pharmacol., 44:33–89(1998), there is great interest and research of therapeutic PDE4 inhibitors.

International Patent Publication WO9422852 describes quinolines as PDE4 inhibitors.

A. H. Cook, et al., J. Chem. Soc., 413–417(1943) describes gamma-pyridylquinolines. Other quinoline compounds are described in Kei Manabe et al., J. Org. Chem., 58(24):6692–6700(1993); Kei Manabe et al., J. Am. Chem. Soc., 115(12):5324–5325(1993); and Kei Manabe et al., J. Am. Chem. Soc., 114(17):6940–6941(1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects. Further there remains a need for efficient processes to produce compounds that therapeutically inhibit PDE4.

SUMMARY OF THE INVENTION

The present invention is directed to a process to synthesize 6-[1-methyl-1-(methylsulfonyl)ethyl]-8-[3-[(E)-2-[3-methyl-1,2,4-oxadiazol-5-yl]-2-[4-(methylsulfonyl)phenyl]ethenyl]phenyl]quinoline and its benzenesulfonic acid salt.

DETAILED DESCRIPTION OF THE INVENTION

Figure 1:
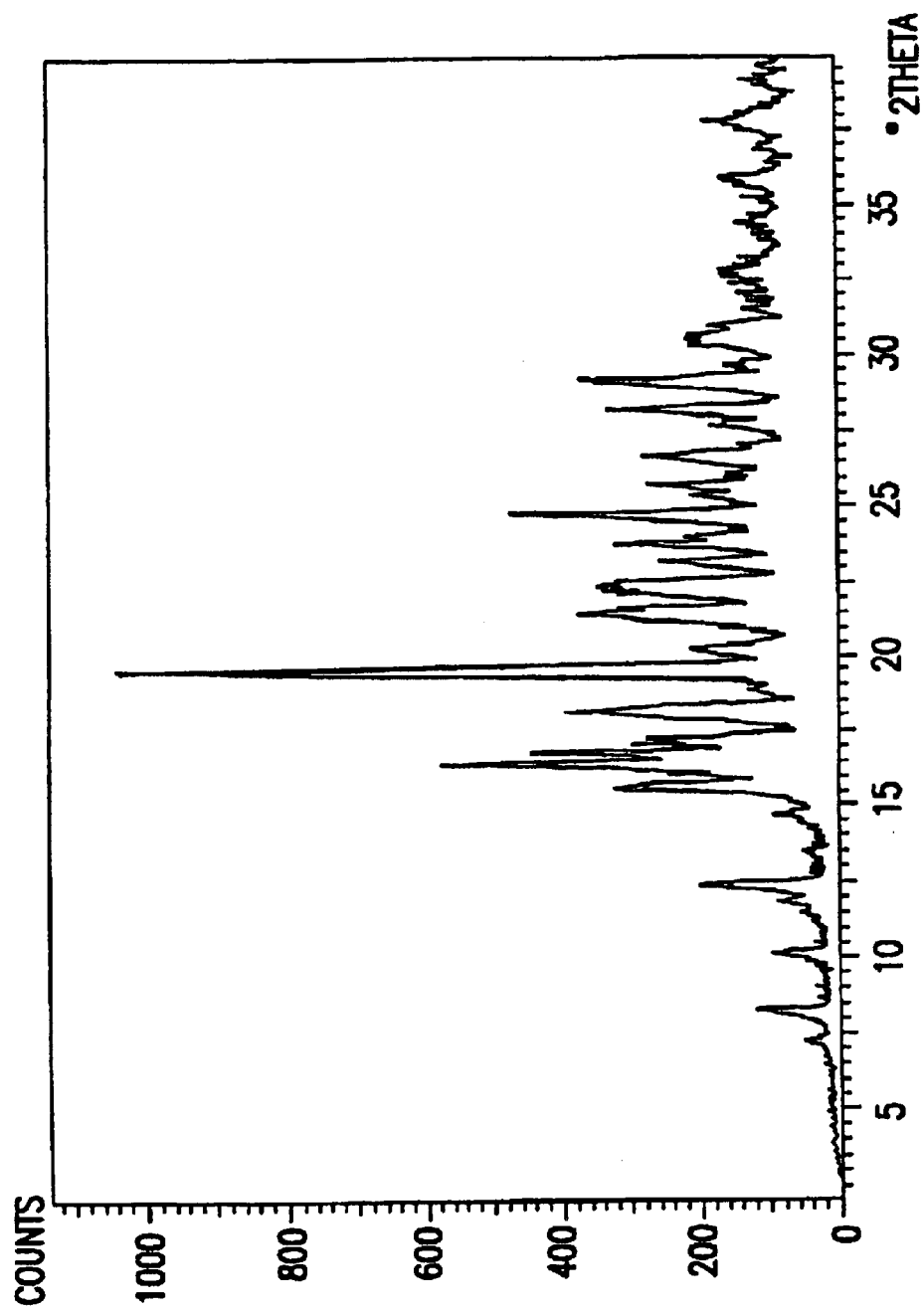
FIG. 1 is a graph of Counts against °Theta for an X-ray Powder Diffraction of the Form A polymorph of the benzenesulfonic acid salt of 6-[1-methyl-1-(methylsulfonylethyl]-8-[3-[(E)2-[3-methyl-1,2,4-oxadiazol-5-yl]-2-[4-(methylsulfonyl)phenyl]ethenyl]phenyl]quinoline.

The present invention forms the compound (the "free base")

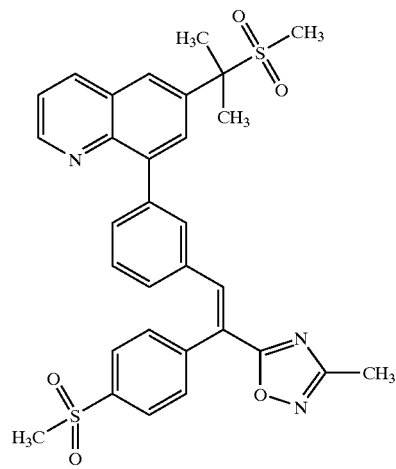

6-[1-methyl-1-(methylsulfonyl)ethyl]-8-[3-[(E)-2-[3-methyl-1,2,4-oxadiazol-5-yl]-2-[4-(methylsulfonyl) phenyl]ethenyl]phenyl]quinoline by the following process:

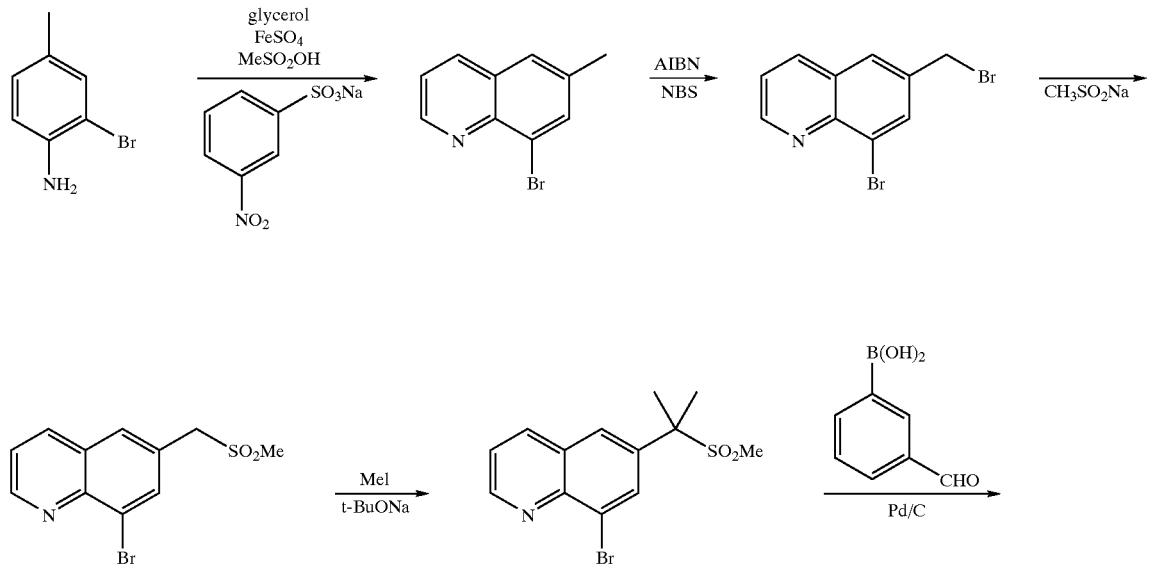

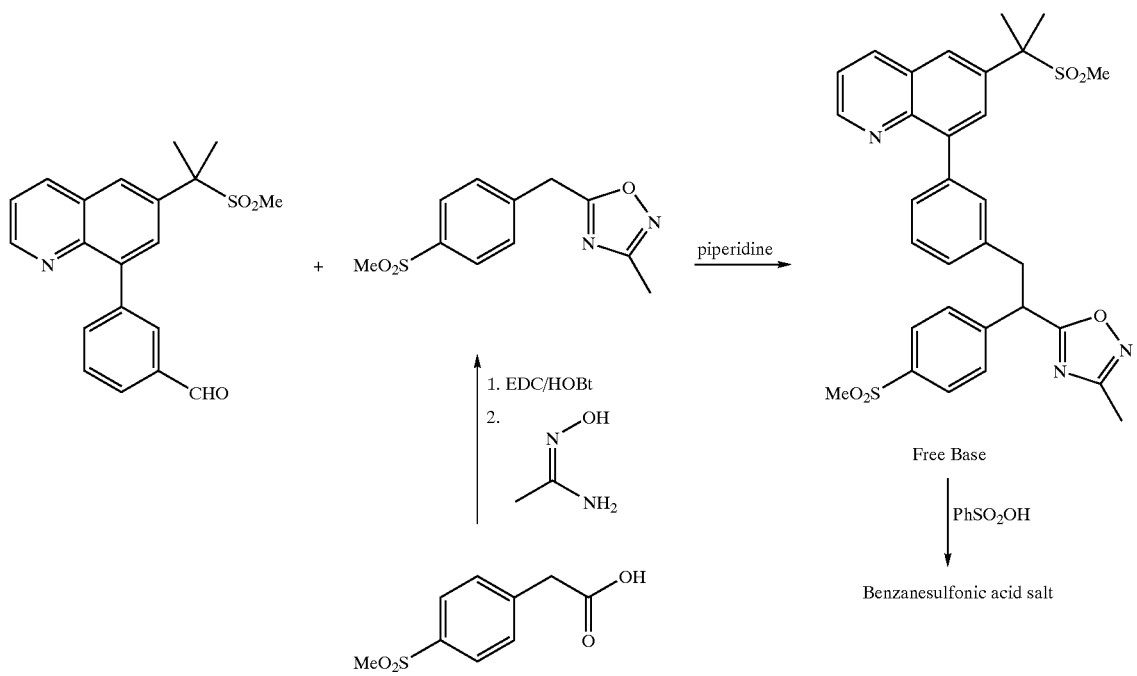

Free Base

↓ PhSO₂OH

Benzanesulfonic acid salt

Step 1. Skraup Reaction

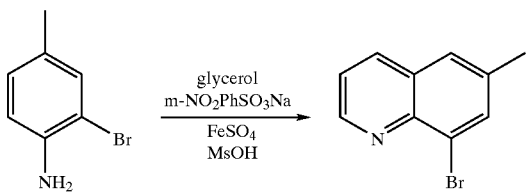

To methanesulfonic acid (8–10 equiv) at 20° C. was added sodium m-nitrobenzenesulfonate (0.6–0.8 equiv), followed by iron sulfate heptahydrate (0.01–0.05 equiv). To the resulting mixture was added 2-bromo-4-methylaniline (1 equiv).

Glycerol (2–3 equiv) was added and the resulting solution was heated at 120–140° C. and aged until the reaction was complete.

The mixture was cooled to 70–90° C. and diluted with water. The solution was then cooled to about 20° C. and neutralized with aqueous NaOH and sodium bicarbonate. MTBE (methyl t-butyl ether) was added and the mixture was filtered and the phases were separated (the product was in the NME layer).

Step 2. Bromination

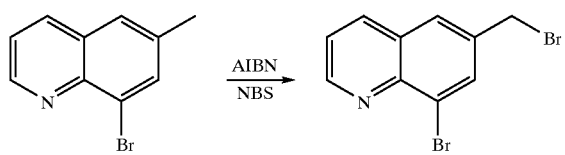

The MTBE solution from step 1 was solvent switched to chlorobenzene. After filtered through Silica gel and partially concentrated, N-bromosuccinimide (NBS, 0.6–0.8 equiv) and 2,2'-azobisisobutylnitrile (AIBN, 0.01–0.1 equiv) were added. The degassed mixture was heated at 55–85° C. The resulting mixture was diluted with cyclohexane. Additional NBS (0.3–0.5 equiv) and AIBN (0.01–0.05 equiv) were added. The degassed mixture was heated at about 55–85° C. until the reaction was completed. The mixture was cooled at 10–40° C. and diluted with cyclohexane and aged. The solid was isolated by filtration.

Step 3. Sulfone Formation

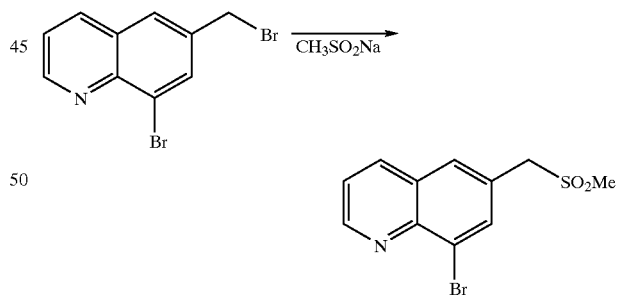

To a solution of bromomethyl-bromoquinoline (product from previous step, 1 equiv) in DMF was added powdered sodium methanesulfinate (1.0–1.5 equiv) at 10–60° C. The mixture was heated at about 50–70° C. for 30 min. The mixture was diluted with water while maintaining temp at about 50–70° C. with vigorous stirring, then cooled to about 10–20° C. and aged. The mixture was filtered and the solid washed sequentially with 1:4 DMF/water and then water and dried.

Step 4. Methylation

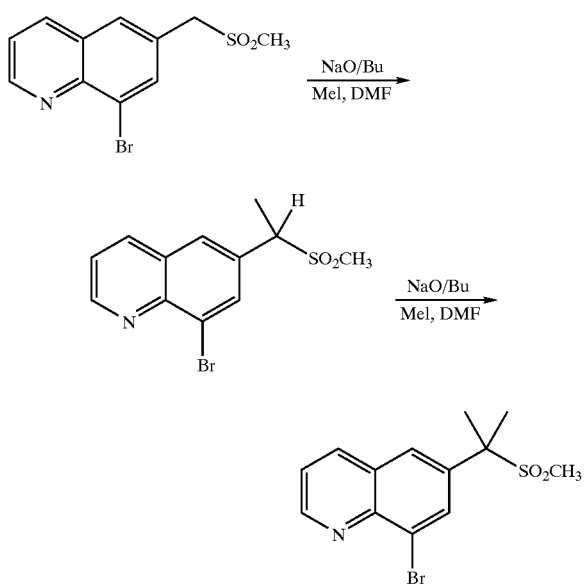

A solution of the sulfone (product from the previous step, 1 equiv) in DMF was cooled to about −10 to 0° C. Sodium t-butoxide (~1 equiv) was added. A solution of methyl iodide/DMF solution (~1 equiv of MeI) was added slowly while maintaining temperature at about −10 to 0° C.

A second portion of solid sodium t-butoxide (~1 equiv) was added, followed by methyl iodide/DMF solution (~1 equiv) was added while maintaining the temperature at −5 to 10° C. (Additional base and MeI may be added if the reaction was not completed). The reaction was quenched by adition of water and the product crystallized, which was isolated and dried.

Step 5. Suzuki Coupling

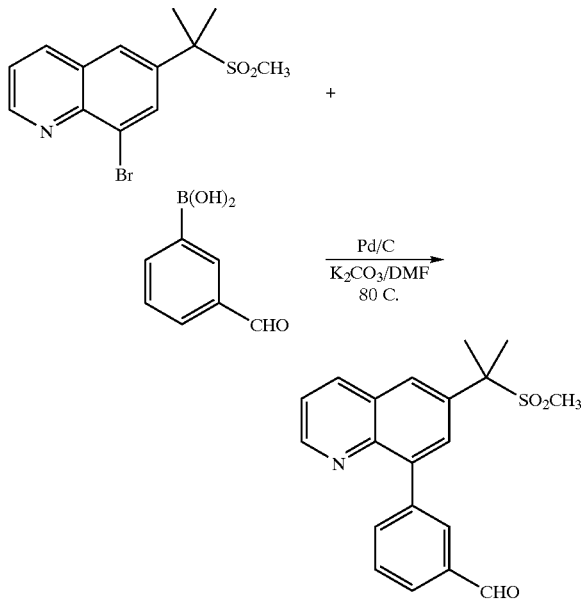

To a solution of the sulfone from the previous step (1 equiv) was added Pd/C (5 or 10 w %, 0.005–0.1 equiv), potassium carbonate (2–3 equiv), and 3-formyl phenylboronic acid (1–2 equiv). The degassed reaction mixture was heated at 60–120° C. until the reaction was complete. The mixture was filtered and the filtrate was diluted with water. The product crystallized and was isolated by filtration and dried.

Step. 6 Oxadiazole

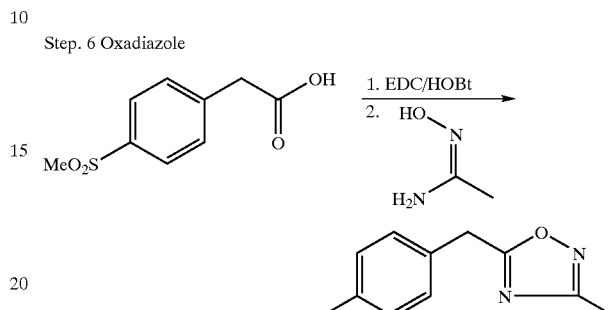

To the mixture of Hydroxy benzotiazole ("HOBt") hydrate (1–1.5 equiv), 4-methylsulfonylphenylacetic acid (1 equiv) in acetonitrile was added EDC hydrochloride (1–1.5 equiv). The slurry was aged at about 20–30° C. for 30 min.

Other N—OH compounds, such as N-hydroxyphthalimide, 2-hydroxypyridine N-oxide, N-hydroxysuccininmide, can also be used to replace HOBt. Other carbodiimides, such as dicyclohexylcarbodiimide and diisopropylcarbodiimide can be used to replace EDC hydrochloride (ethyl dimethylaminopropylcarbodiimide hydrochloride).

To the slurry was added acetamide oxime (1–1.5 equiv). The resulting mixture was then heated at reflux until the reaction was complete. The resulting solution was concentrated and diluted with ethyl acetate. To the resulting mixture was washed with aqueous sodium bicarbonate. The solution was solvent switched to 2-propanol and product crystallized upon cooling, which was isolated and dried.

Step 7. Condensation to form the Free Base Compound

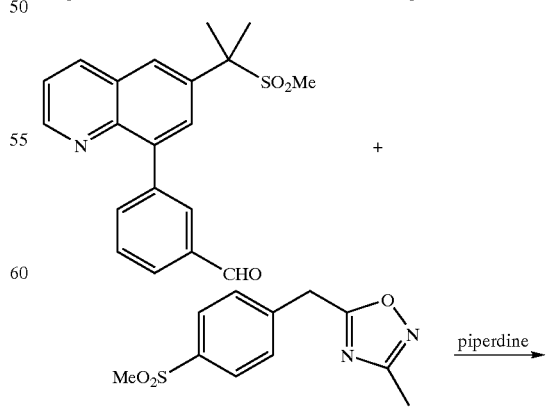

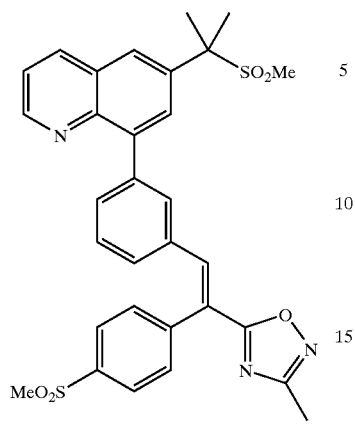

To a slurry of the aldehyde from step 5 above (1 equiv) in 2-propanol was added the oxadiazole from step 6 above (1–1.5 equiv), followed by piperidine (0.2–1.5 equiv).

In place of 2-propanol, other solvents such as, for example, DMF, acetonitrile, 1-propanol, toluene, esters, and other alcohols. Piperidine serves as a basic initiator. In place of piperidine, other amine bases, especially secondary amines, can be used.

The resulting mixture was heated at reflux over molecular sieves until the reaction was completed. After cooling, the product was isolated by filtration and dried.

The benzenesulfonic acid salt of the Free Base compound is available in two crystalline forms ("Form A" and "Form B"). The forms are produced by the following procedures:

Step 8. Salt Formation

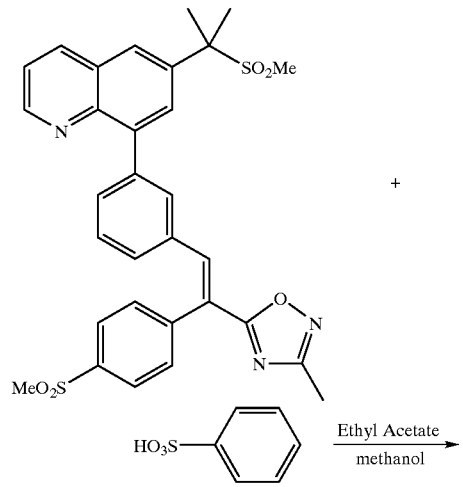

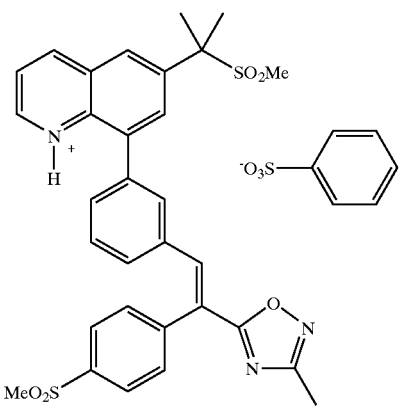

Form A

To a slurry of the Free Base from step 7 above (1 equiv) in ethyl acetate was added benzenesulfonic acid (1–1.2 equiv). Other esters may be used in place of ethyl acetate. Methanol was added and the resulting mixture was heated until the solid dissolved. Other alcohols such as ethanol or propanol may be used in place of the methanol.

The resulting solution was filtered and concentrated. The product crystallized during concentration. The resulting mixture was diluted with ethyl acetate and aged. The yellow solid was collected by filtration.

HPLC indicated a 1:1 molar ratio of 6-[1-methyl-1-(methylsulfonyl)ethyl]-8-[3-[(E)-2-[3-methyl-1,2,4-oxadiazol-5-yl]-2-[4-(methylsulfonyl)phenyl]ethenyl]phenyl]quinoline and benzenesulfonic acid.

m.p. by DSC: 193° C.

Figure 4:
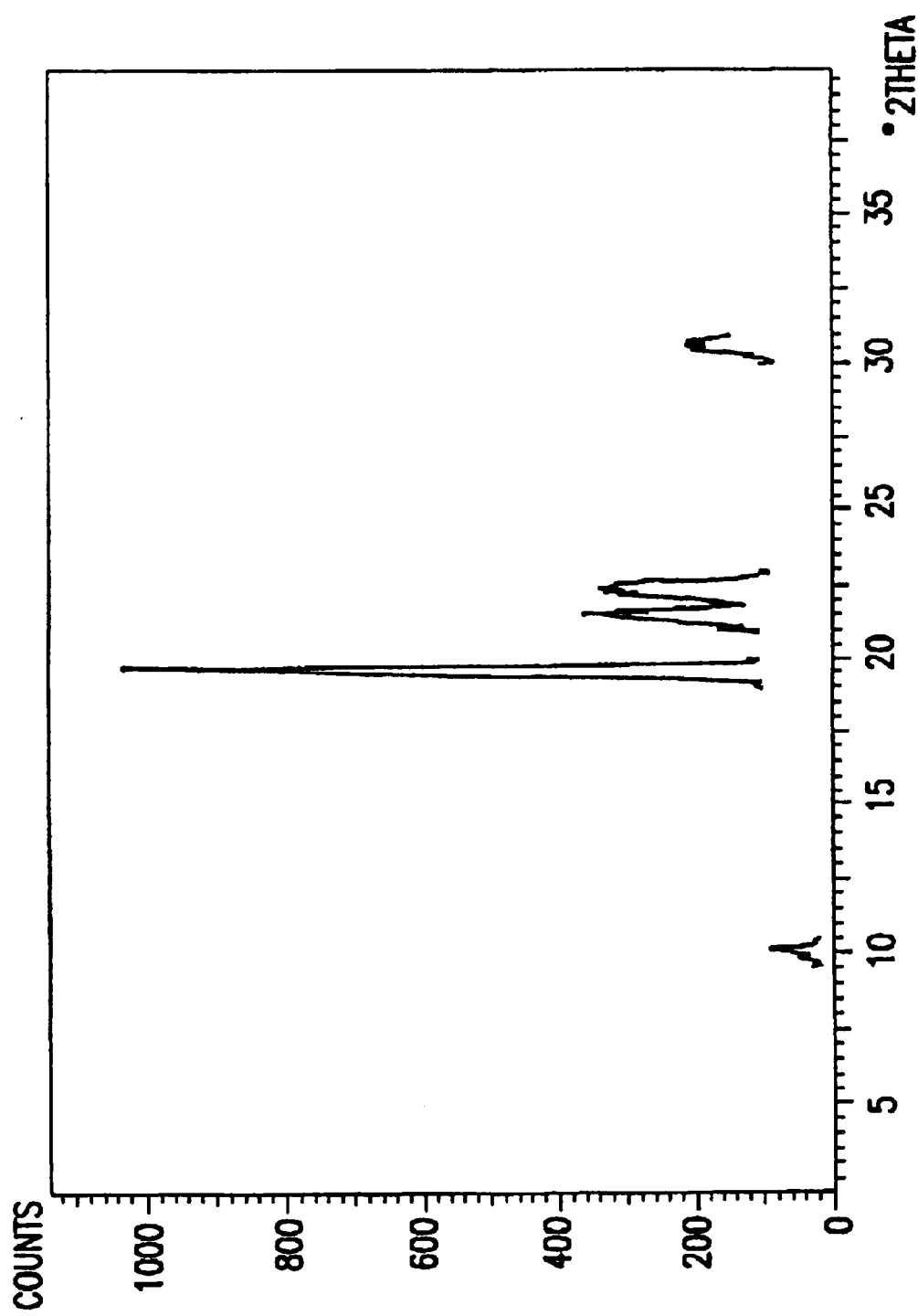
FIG. 4 is a graph of the distinguishing feature peaks of the X-ray Powder Diffraction of the Form A polymorph of the benzenesulfonic acid salt of 6-[1-methyl-1-(methylsulfonyl) ethyl]-8-[3-[(E)-2-[3-methyl-1,2,4-oxadiazol-5-yl]-2-[4-(methylsulfonyl)phenyl]ethenyl]phenyl]quinoline.

The X-ray Powder Diffraction ("XRPD") Spectrogram for the Form A is shown in FIG. 1. The identifying peaks are tabulated below and shown in FIG. 4.

| Peaks Identifying Form A Polymorph (°2Theta) |
| --- |
| 10.0 |
| 19.5 |
| 21.4 |
| 22.4 |
| 30.5 |

Form B

To a slurry of the Free Base from step 7 above (1 equiv) in a mixture of isopropyl acetate (i-PrOAc) and methanol (1:1) was added benzenesulfonic acid (1–1.2 equiv). Other esters may be used in place of i-PrOAc and other alcohols such as ethanol or propanol may be used in place of methanol. The mixture was aged at 20–50° C. until the solids dissolved. The resulting solution was filtered and distilled while the volume was maintained by addition of a 9:1 (v/v) mixture of i-PrOAc/methanol. The product crystallized during the distillation.

The resulting mixture was aged at 20–70° C. for 2–10 h to ensure complete formation of Form B. The resulting off-white solid was isolated by filtration and dried.

HPLC indicated a 1:1 molar ratio of 6-[1-methyl-1-(methylsulfonyl)ethyl]-8-[3-[(E)-2-[3-methyl-1,2,4-oxadiazol-5-yl]-2-[4-(methylsulfonyl)phenyl]ethenyl]phenyl]quinoline and benzenesulfonic acid.

m.p. by DSC: 210° C.

Figure 2:
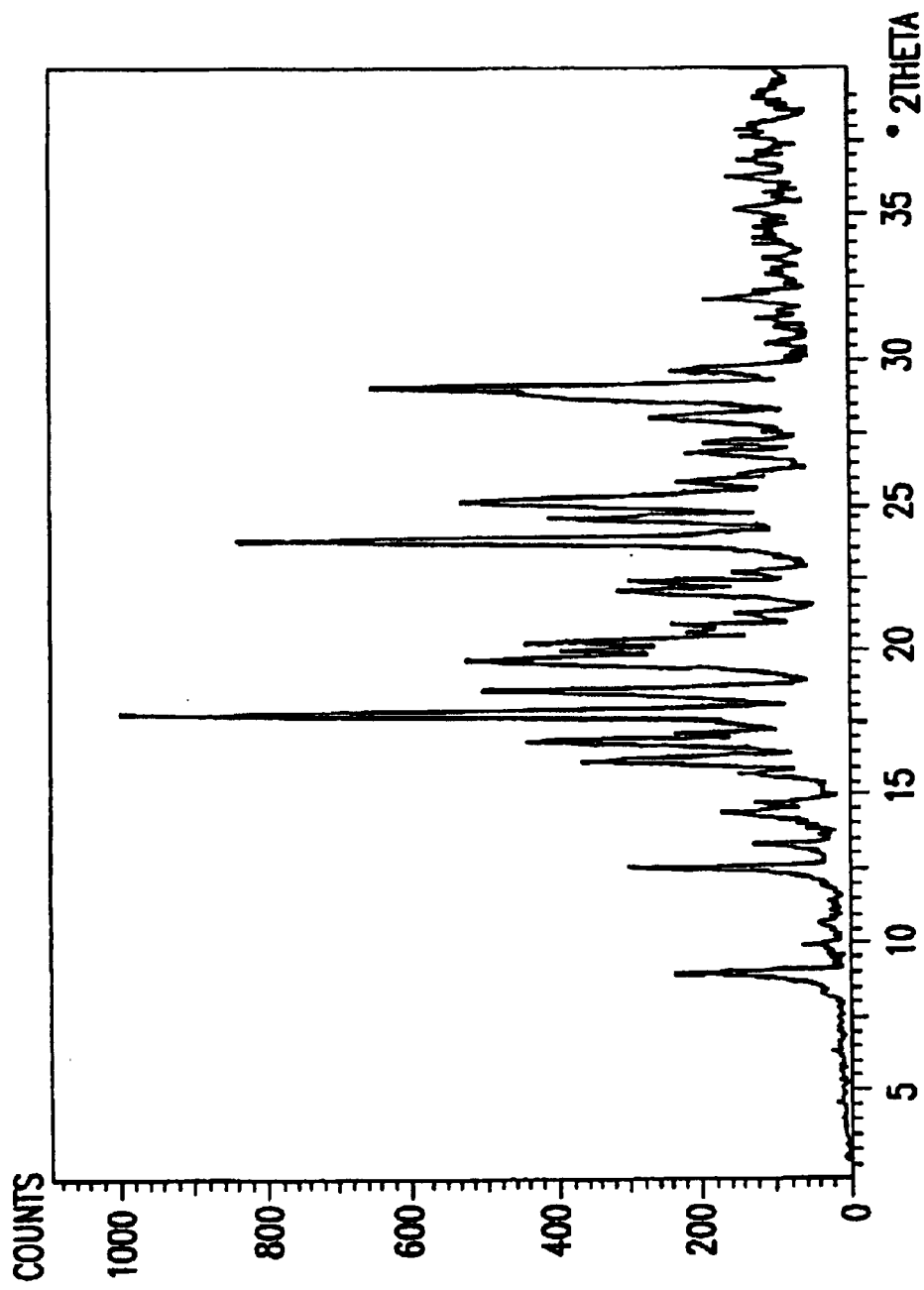
FIG. 2 is a graph of Counts against °Theta for an X-ray Powder Diffraction of the Form B polymorph of the benzenesulfonic acid salt of 6-[1-methyl-1-(methylsulfonyl) ethyl]-8-[3-[(E)2-[3-methyl-1,2,4-oxadiazol-5-yl]-2-[4-(methylsulfonyl)phenyl]ethenyl]phenyl]quinoline.
Figure 3:
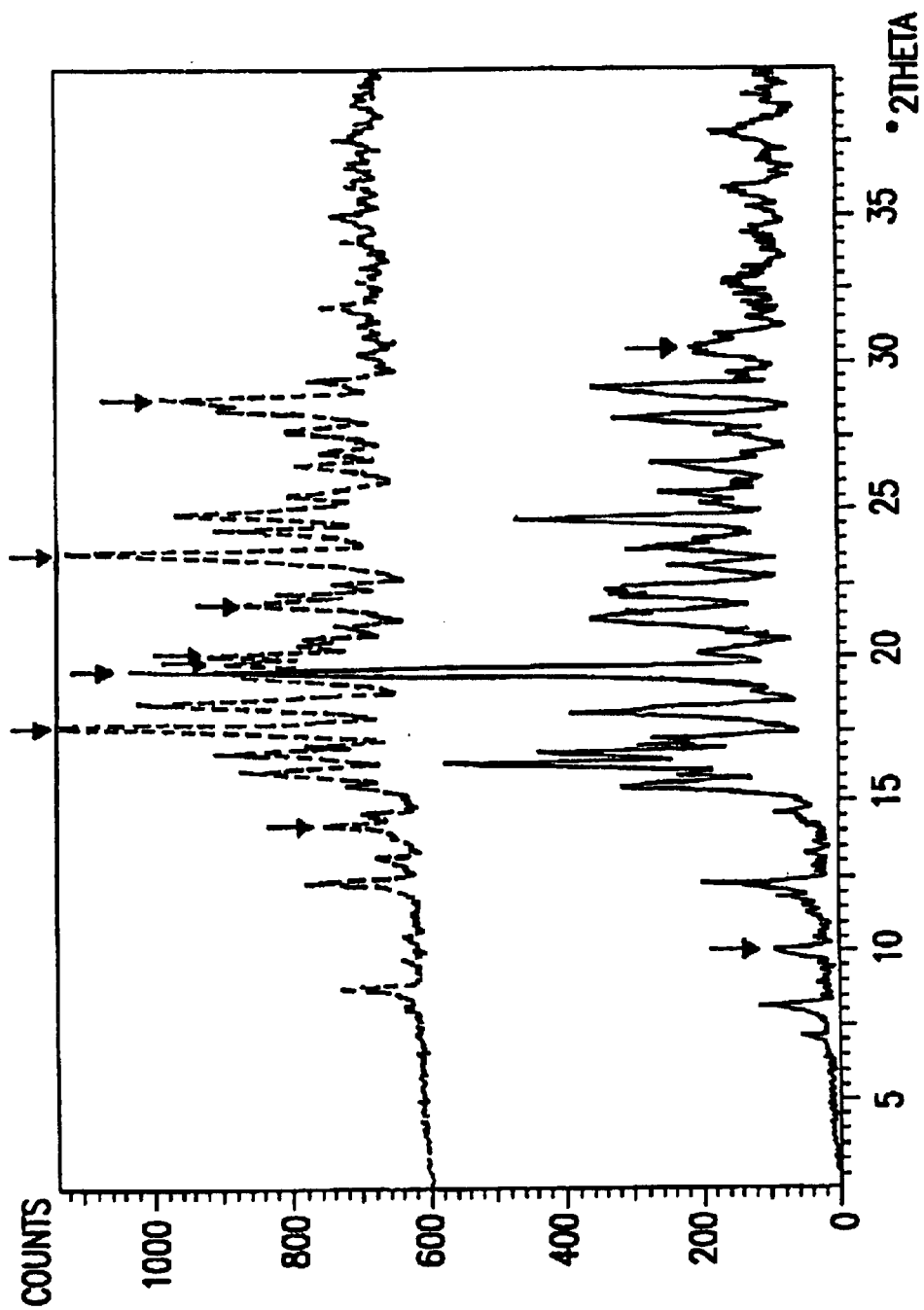
FIG. 3 is a comparison of the X-ray Powder Diffractions of the Form A polymorph (bottom trace) and the Form B (upper trace) of the benzenesulfonic acid salt of 6-[1-methyl-1-(methylsulfonyl)ethyl]-8-[3-[(E)-2-[3-methyl-1,2,4-oxadiazol-5-yl]-2-[4-(methylsulfonyl)phenyl]ethenyl] phenyl]quinoline.
Figure 5:
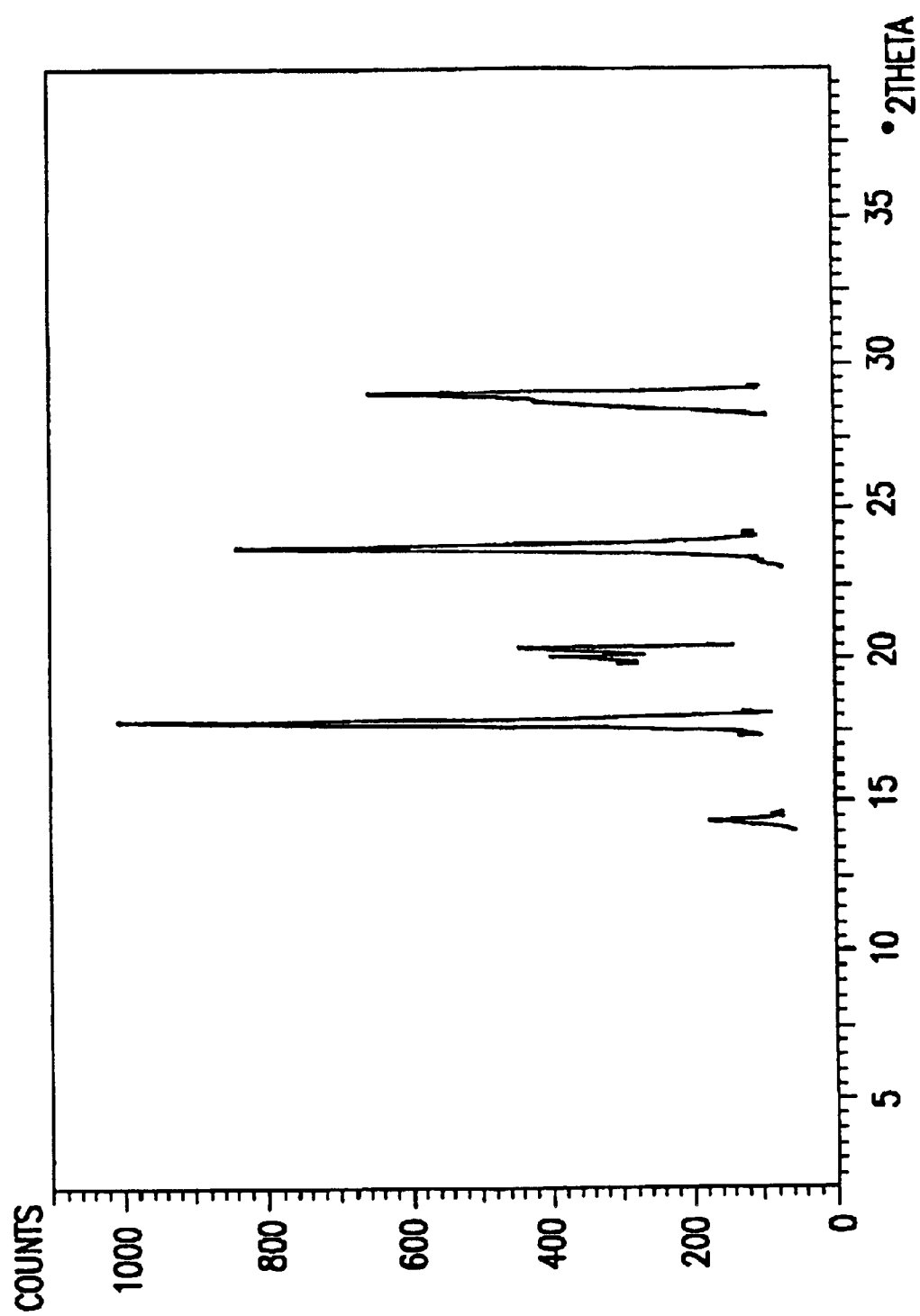
FIG. 5 is a graph of the distinguishing feature peaks of the X-ray Powder Diffraction of the Form B polymorph of the benzenesulfonic acid salt of 6-[1-methyl-1-(methylsulfonyl) ethyl]-8-[3-[(E)2-[3-methyl-1,2,4-oxadiazol-5-yl]-2-[4-(methylsulfonyl)phenyl]ethenyl]phenyl]quinoline.

The XRPD Spectrogram for the Form B is shown in FIG. 2. The identifying peaks are tabulated below and shown in FIG. 5. The spectra are compared in FIG. 3 with the identifying peaks pointed out by arrows.

| Peaks Identifying Form B Polymorph (°2Theta) |
|---|
| 14.4 |
| 17.7 |
| 20.0 |
| 20.2 |
| 23.7 |
| 28.9 |

What is claimed is:

1. A method of forming a reaction product mixture substantially containing a benzenesulfonic acid salt of compound (I) characterized by X-ray Powder Diffraction peaks at 10.0, 19.5, 21.4, 22.4 and 30.5:

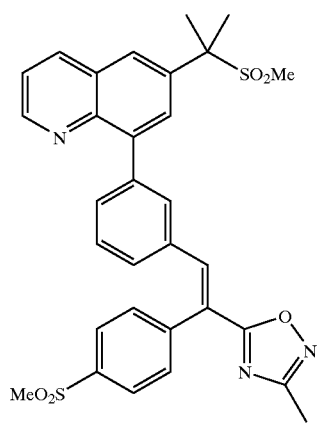
(I)

said method comprising adding an effective amount of benzenesulfonic acid to a mixture of compound (I) in an effective amount of a ester solvent to form a reaction mixture;

adding an effective amount of a alcoholic solvent to said reaction mixture to form a reaction solution;

causing crystallization effective to form crystals characterized by X-ray Powder Diffraction peaks at 10.0, 19.5, 21.4, 22.4, and 30.5.

2. A method of forming a reaction product mixture substantially containing a benzenesulfonic acid salt of compound (I) characterized by X-ray Powder Diffraction peaks at 14.4, 17.7, 20.0, 20.2, 23.7, and 28.9:

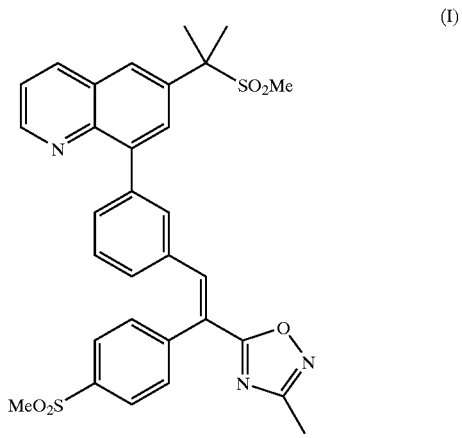
(I)

said method comprising:

adding an effective amount of benzenesulfonic acid to a mixture of compound (I) in an effective amount of an about equivolume mixture of a solvent ester and a solvent alcohol to form a reaction mixture;

causing the solids in said reaction mixture to dissolve to form a reaction solution;

causing crystallization effective to form crystals characterized by X-ray Powder Diffraction peaks at 14.4, 17.7, 20.0, 20.2, 23.7, and 28.9.

* * * * *